United States Patent
Carey (10) Patent No.: US 10,370,595 B2
(45) Date of Patent: Aug. 6, 2019

(54) SYSTEM FOR AND METHOD OF USING ON-SITE EXCESS HEAT TO CONVERT $CO_2$ EMISSIONS INTO HYDROCARBONS INCOME AT COAL-FIRED POWER PLANTS

(71) Applicant: Marine Power Products Incorporated, Hayward, CA (US)

(72) Inventor: Jeffrey M. Carey, Hayward, CA (US)

(73) Assignee: Marine Power Products Incorporated, Hayward, CA (US)

( * ) Notice: Subject to any disclaimer, the term of this patent is extended or adjusted under 35 U.S.C. 154(b) by 0 days.

(21) Appl. No.: 13/796,854

(22) Filed: Mar. 12, 2013

(65) Prior Publication Data

US 2013/0245136 A1   Sep. 19, 2013

Related U.S. Application Data

(60) Provisional application No. 61/610,423, filed on Mar. 13, 2012.

(51) Int. Cl.
| | |
|---|---|
| *B01J 8/00* | (2006.01) |
| *C10G 2/00* | (2006.01) |
| *C07C 29/151* | (2006.01) |
| *C10G 3/00* | (2006.01) |

(52) U.S. Cl.
CPC ............ *C10G 2/50* (2013.01); *B01J 8/00* (2013.01); *C07C 29/1518* (2013.01); *C10G 3/50* (2013.01); *C01B 2203/061* (2013.01); *C01B 2203/062* (2013.01); *C01B 2203/063* (2013.01); *C10G 2400/02* (2013.01); *C10G 2400/04* (2013.01); *C10G 2400/08* (2013.01); *C10J 2300/1659* (2013.01); *C10J 2300/1665* (2013.01); *Y02E 60/36* (2013.01); *Y02P 30/10* (2015.11); *Y02P 30/20* (2015.11)

(58) Field of Classification Search
None
See application file for complete search history.

(56) References Cited

U.S. PATENT DOCUMENTS

| | | | |
|---|---|---|---|
| 3,954,592 | A | 5/1976 | Horvath |
| 4,004,067 | A | 1/1977 | Briggs et al. |
| 4,144,147 | A | 3/1979 | Jarrett et al. |
| 4,358,291 | A | 11/1982 | Cuomo et al. |

(Continued)

FOREIGN PATENT DOCUMENTS

| | | |
|---|---|---|
| CN | 101160258 A | 4/2008 |
| EP | 1249052 B1 | 4/2009 |

(Continued)

OTHER PUBLICATIONS

Machine translation for EP 2360230 A1 (Aug. 2011).*

(Continued)

*Primary Examiner* — Jennifer A Leung
(74) *Attorney, Agent, or Firm* — Haverstock & Owens LLP (57) ABSTRACT

A solution is provided for $CO_2$ and other green houses gas reduction at the Coal Fired Power Plants (CFPP). The methods and devices disclosed herein provide an inexpensive source of hydrogen and a hydrogen generating system powered by on-site excess heat generated at the CFPP without producing additional $CO_2$ emission.

14 Claims, 4 Drawing Sheets

(56) References Cited

U.S. PATENT DOCUMENTS

| | | | |
|---|---|---|---|
| 4,394,293 | A | 7/1983 | Gratzel et al. |
| 4,454,427 | A | 6/1984 | Sosnowski et al. |
| 5,219,671 | A | 6/1993 | Parker et al. |
| 5,796,799 | A | 8/1998 | Kobayashi et al. |
| 6,306,917 | B1 | 10/2001 | Bohn et al. |
| 6,843,903 | B2 | 1/2005 | Roe et al. |
| 6,991,719 | B2 | 1/2006 | Ovshinsky |
| 7,125,480 | B2 | 10/2006 | Austin |
| 7,178,339 | B2 | 2/2007 | Goldmeer et al. |
| 7,252,806 | B1 | 8/2007 | Merritt |
| 7,875,166 | B2 | 1/2011 | Matthai et al. |
| 7,989,507 | B2 | 8/2011 | Rising |
| 2001/0046113 | A1 | 11/2001 | Schmidt |
| 2002/0048548 | A1 | 4/2002 | Chaklader |
| 2002/0155330 | A1 | 10/2002 | Tanaka |
| 2004/0265678 | A1 | 12/2004 | Hommura et al. |
| 2005/0051439 | A1 | 3/2005 | Jang |
| 2005/0269211 | A1 | 12/2005 | Lachar |
| 2006/0102468 | A1 | 6/2006 | Monzyk et al. |
| 2006/0118428 | A1 | 6/2006 | Baltrucki et al. |
| 2006/0180464 | A1 | 8/2006 | Griffin |
| 2006/0188436 | A1 | 8/2006 | Griffin |
| 2006/0249393 | A1 | 11/2006 | Ghosh et al. |
| 2007/0072949 | A1 | 3/2007 | Ruud et al. |
| 2007/0244208 | A1 | 10/2007 | Shulenberger et al. |
| 2008/0296172 | A1 | 12/2008 | Davidson |
| 2009/0074611 | A1 | 3/2009 | Monzyk et al. |
| 2009/0101520 | A1 | 4/2009 | Zhang et al. |
| 2009/0110976 | A1 | 4/2009 | Yoshida et al. |
| 2009/0115190 | A1 | 5/2009 | Devine |
| 2009/0152126 | A1 | 6/2009 | Griffin |
| 2009/0277799 | A1 | 11/2009 | Grimes |
| 2010/0000874 | A1 | 1/2010 | Hinman et al. |
| 2010/0004495 | A1* | 1/2010 | Fareid et al. ......... 585/310 |
| 2010/0005809 | A1 | 1/2010 | Anderson |
| 2010/0133111 | A1 | 6/2010 | Nocera et al. |
| 2010/0224502 | A1 | 9/2010 | Carey |
| 2011/0041740 | A1* | 2/2011 | Reilly ......... 110/341 |
| 2011/0114075 | A1 | 5/2011 | Mills |
| 2013/0277231 | A1 | 10/2013 | Greenberg |
| 2013/0281553 | A1* | 10/2013 | Kubic et al. ......... 518/702 |

FOREIGN PATENT DOCUMENTS

| | | | | |
|---|---|---|---|---|
| EP | 2360230 | A1 * | 8/2011 | |
| GB | 2461723 | A * | 1/2010 | ......... C07C 29/1518 |
| WO | 8910981 | | 11/1989 | |
| WO | 2010084358 | A2 | 7/2010 | |
| WO | WO 2011002527 | A1 * | 1/2011 | |
| WO | WO 2012062529 | A2 * | 5/2012 | |

OTHER PUBLICATIONS

Hydrogen Production-Wikepedia, the free encyclopedia, pp. 4-7, http://en.wikipedia.org/wiki/Hydrogen_production, retrieved Dec. 12, 2008.

Venere,Emil, "New Process Generates Hydrogen From Aluminum Alloy to Run Engines, Fuel Cells", Purdue University, http://news.uns.purdue.edu/x/2007a/070515WoodallHydrogen.html, May 15, 2007.

Perret, Robert, "II.F.1 Develpment of Solar-Powered Thermochemical Production of Hydrogen from Water", DOE Hydrogen Program, FY 2007 Annual Progress Report, pp. 128-135.

Kim, MingJoong et al., "Hydrogen generation from hydrolysis reaction through corrosion of Al—Cu alloy in alkaline Water", Dep. of Materail Science and Engineering, Korea Advanced Institute of Science and Technology.

"Bayer process", hhtp://en.wikipedia.org/wiki/Bayer_proces, pp. 1-2, Retrieved Dec. 13, 2007.

Soler, Lluis et al., "Aluminum and aluminum alloys as sources of hydrogen for fuel cell applications", Journal of Power Sources,2007, www.sciencedirect.com, www.elsevier.com/locate/jpowsour, pp. 144-149.

Currao et al., Water Splitting with Silver Chloride Photoanodes and Amorphous Silicon solar Cells. Photochemical and Photobiological Sciences, vol. 3, 2004, [retrieved on Nov. 19, 2013], Retrieved from the Internet. <URL: http://www.gioncalzaferri.ch/publikationen/Photochem_Photobiol_Sci_2004_3_1017%20Watersplitting.pdf>, entire document.

Peters, W.G., "Colloidal Silver Chemistry", http://www.wgpeters.com/colloidal-silver-chemistry//, pp. 1-3, May 8, 2010.

Frederick Lowenheim, "Electroplating", McGraw-Hill Book Company, New York 1979, p. 12-25.

David R. Lide et al., "CRC Handbook of Chemistry and Physics 76th Eddition", New York 1195-1996, p. 8-58.

Kanoglu et al., "Thermodynamic Analysis of Models used in Hydrogen Production by Geothermal Energy", International Journal of Hydrogen Energy, vol. 35, 2010, pp. 8783-8791.

Hand, Theodore, W., "Hydrogen Production Using Geothermal Energy" (2008), All Graduate Theses and Dissertations, Paper 39, accessed at http://digitalcommons.usu.edu/etd/39 on Apr. 16, 2016.

"The Jet Engine", Third Edition, Rolls-Royce Limited, 1969, pp. 9-14.

\* cited by examiner

SYSTEM FOR AND METHOD OF USING ON-SITE EXCESS HEAT TO CONVERT $CO_2$ EMISSIONS INTO HYDROCARBONS INCOME AT COAL-FIRED POWER PLANTS

CROSS-REFERENCE TO RELATED APPLICATION(S)

This application claims priority under 35 U.S.C. § 119(e) of the U.S. Provisional Patent Application Ser. No. 61/610,423, filed Mar. 13, 2012 and titled, "USE ON-SITE EXCESS HEAT TO CONVERT $CO_2$ EMISSIONS INTO HYDROCARBONS INCOME AT COAL-FIRED POWER PLANTS," which is hereby incorporated by reference in its entirety for all purposes.

FIELD OF THE INVENTION

The present invention relates to the field of energy conversion. More specifically, the present invention relates to carbon dioxide conversion and usage.

BACKGROUND OF THE INVENTION

Conventional industry produces hydrogen using processes known as Steam Reformation, Partial Oxidation (PDX), and Autothermal Reforming (ATR). These processes use natural gas and steam to produce hydrogen. However, since these processes also create $CO_X$ (x=1, 2), the effectiveness and cleanliness of this hydrogen are questionable because the hydrogen producing systems are also carbon emission/generating sources.

SUMMARY OF THE INVENTION

In some embodiments, the present invention provides a solution for $CO_2$ and other green house gas reduction at the Coal Fired Power Plants (CFPP). The methods and devices disclosed herein provide an inexpensive source of hydrogen and provide a hydrogen producing system powered by on-site excess heat generated at the CFPP without producing additional $CO_2$ emission.

In an aspect, a system for producing a hydrocarbon compound comprising a hydrogen producing unit, a furnace producing heat and carbon dioxide, and a hydrocarbon converter, wherein the hydrocarbon converter receives the carbon dioxide from the furnace and receives hydrogen from the hydrogen producing unit. In some embodiments, the furnace comprises a coal fired power plant. In other embodiments, the furnace comprises a coal-combustor. In some other embodiments, the system further comprises a $CO_2$-to-methanol converter. In some embodiments, the hydrocarbon converter comprises a methanol-to-gasoline converter. In other embodiments, the hydrocarbon converter receives hydrogen from the hydrogen producing unit. In some other embodiments, the hydrocarbon converter comprises a Fischer-Tropsch processing unit. In some embodiments, the hydrocarbon converter comprises a paraffin producing unit. In some other embodiments, the hydrocarbon converter comprises a naphtha, kerosene, or diesel producing unit. In some embodiments, the furnace receives oxygen from the hydrogen producing unit. In some embodiments, the hydrogen producing unit generates hydrogen. In other embodiments, the heat generates heated water to be supplied to the hydrogen producing unit. In some other embodiments, the hydrogen producing unit comprises an aluminum compound based catalytic system. In some embodiments, the aluminum compound based catalytic system comprises aluminium compound, copper compound, and silver compound. In other embodiments, the aluminum compound based catalytic system comprises aluminium hydroxide, copper hydroxide, and silver hydroxide.

In another aspect, a method of producing a hydrocarbon compound comprising generating hydrogen and oxygen using an aluminum based catalyst and heat generated at a power plant and converting $CO_2$ generated at the power plant to a hydrocarbon compound. In some embodiments, the aluminum based catalyst comprises aluminium hydroxide, copper hydroxide, and silver hydroxide. In other embodiments, the hydrocarbon compound comprises gasoline. In some other embodiments, the hydrocarbon compound comprises paraffin. In some embodiments, the hydrocarbon compound comprises naphtha, kerosene, or diesel. In other embodiments, the hydrocarbon compound comprises methanol. In some other embodiments, the hydrogen and the oxygen are generated at a hydrogen generating chamber.

In another aspect, a method of mitigating carbon dioxide production comprising generating hydrogen using an aluminium based catalyst at a hydrogen producing unit, combining the hydrogen and substantial all of carbon dioxide generated at a furnace of a power plant, and converting the carbon dioxide to a hydrocarbon compound. In some embodiments, the method further comprises a methanol converter, such that the hydrogen and the carbon dioxide are combined to produce methanol. In other embodiments, the methanol is converted to gasoline at a methanol-to-gasoline converter. In some other embodiments, the methanol-to-gasoline converter receives hydrogen generated at the hydrogen producing unit. In some embodiments, the hydrogen producing unit generates oxygen. In other embodiments, the hydrogen producing unit receives a heated water from a furnace.

Other features and advantages of the present invention will become apparent after reviewing the detailed description of the embodiments set forth below.

BRIEF DESCRIPTION OF THE DRAWINGS

Embodiments will now be described by way of examples, with reference to the accompanying drawings which are meant to be exemplary and not limiting. For all figures mentioned herein, like numbered elements refer to like elements throughout.

DETAILED DESCRIPTION OF THE PREFERRED EMBODIMENT

Reference will now be made in detail to the embodiments of the method and apparatus of the invention, examples of which are illustrated in the accompanying drawings. While the invention is described in conjunction with the embodiments below, it is understood that they are not intended to limit the invention to these embodiments and examples. On the contrary, the invention is intended to cover alternatives, modifications and equivalents, which are included within the spirit and scope of the invention as defined by the appended claims. Furthermore, in the following detailed description of the present invention, numerous specific details are set forth in order to more fully illustrate the present invention. However, it is apparent to one of ordinary skill in the art having the benefit of this disclosure that the present invention is able to be practiced without these specific details. In other instances, well-known methods and procedures, components and processes have not been described in detail so as not to unnecessarily obscure aspects of the present invention. It is, of course, appreciated that in the development of any such actual implementation, numerous implementation-specific decisions must be made in order to achieve the developer's specific goals, such as compliance with application and business related constraints, and that these specific goals are vary from one implementation to another and from one developer to another. Moreover, it is appreciated that such a development effort can be complex and time-consuming, but would nevertheless be a routine undertaking of engineering for those of ordinary skill in the art having the benefit of this disclosure.

About two thirds of the coal energy consumed at the CFPP is lost to the environment in the form of heat. The present invention provides methods and devices to utilize this wasted energy and convert unwanted carbon dioxide to hydrocarbon commodities with a modest capital expense in added Carbon Capture and Utilization (CCU) infrastructure. The hydrocarbon commodities include methanol, ethanol, gasoline, and diesel. The present invention uses waste heat from the CFPP to generate hydrogen and oxygen, which are used to generate hydrocarbons.

Figure 1:
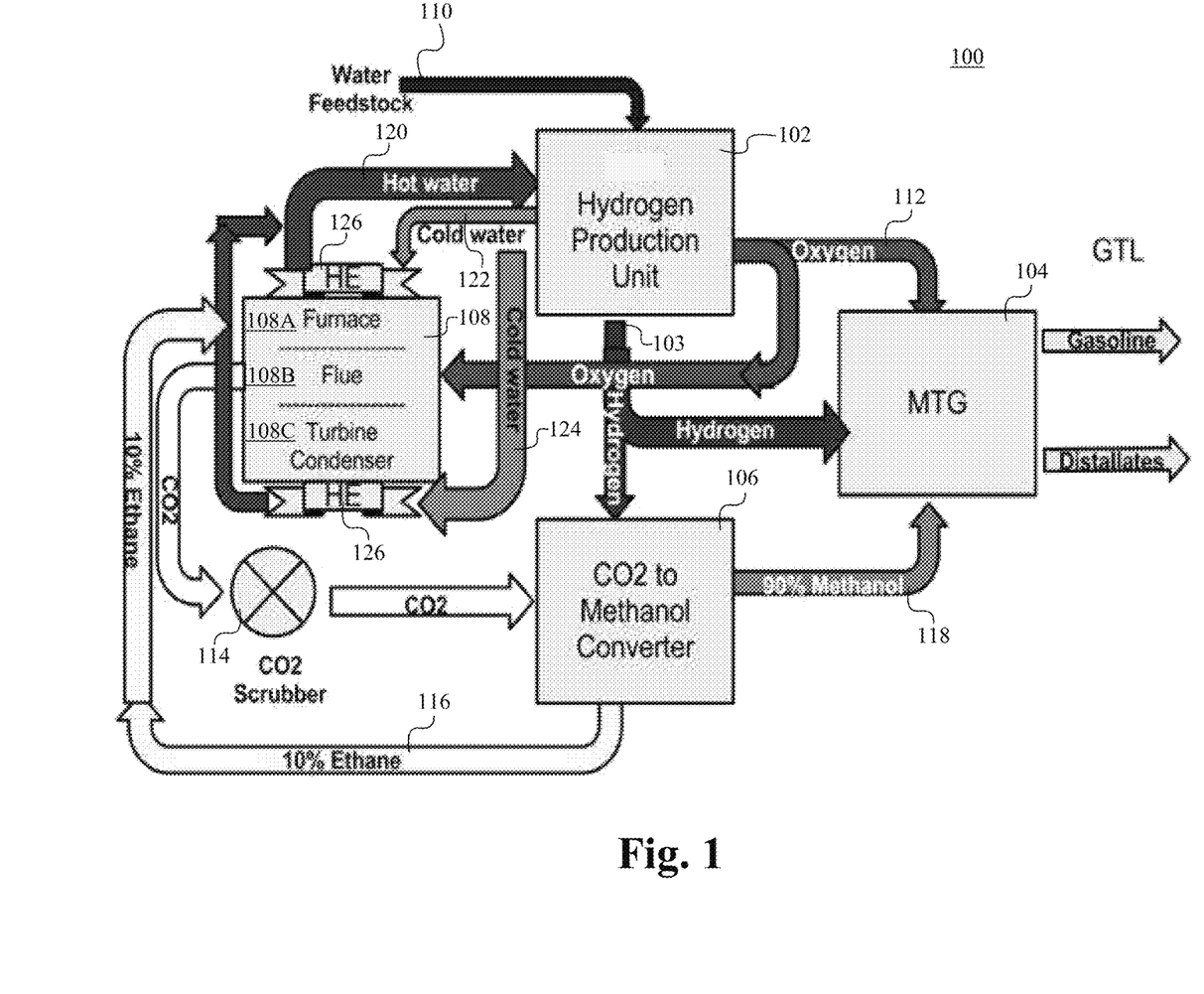
FIG. 1 illustrates a coal fired power plant for converting carbon dioxide to gasoline in accordance with some embodiments of the present invention.

FIG. 1 illustrates a coal fired power plant 100 for converting carbon dioxide to gasoline in accordance with some embodiments of the present invention. The plant 100 comprises a hydrogen production unit 102, a methanol-to-gasoline converter (MTG converter) 104, a $CO_2$-to-methanol converter 106, and a furnace 108. The furnace 108 is able to be a CFPP, which comprises a coal furnace 108A, a chamber area for flue gas 108B, and turbine and condenser 108C for generating electricity. The hydrogen production unit 102 receives water from the water feedstock 110 and generate hydrogen and oxygen via catalytic reactions in the hydrogen production unit 102. The reactants, reaction conditions, and the catalysts for the catalytic reactions are described below. Hydrogen 103 that is generated at the hydrogen generation unit 102 is supplied to the $CO_2$-to-methanol converter 106 and the MTG converter 104. Oxygen 112 that is generated at the hydrogen generation unit 102 is supplied to the furnace 108 and the MTG converter 104. The oxygen 112 that is provided to the furnace 108 facilitates the full oxygenation of COx, which is subsequently supplied to the $CO_2$-to-methanol converter 106 via a $CO_2$ scrubber 114 as a $CO_2$ source. The $CO_2$-to-methanol converter 106 generate about 10% of ethane 116 to be used at the furnace 108 and about 90% of methanol 118 that is supplied to the MTG 104. Hot water 120 from the furnace 108 is supplied to the hydrogen production unit 102 as a heat source. By using the waste heat from the furnace 108 as an energy source to produce hydrogen and oxygen at the hydrogen production unit 102, significant amount of energy is able to be saved. The hot water 120 that is used to heat up the hydrogen production unit 102 becomes cold water 122 and 124, which are used to cool the heat exchanger 126 at the furnace 108.

At the MTG 104, a ZSM-5 zeolite is used to convert methanol, hydrogen, and oxygen to become gasoline. In some embodiments, the methanol-to-gasoline process is able to be a typical methanol-to-gasoline process, such as Mobil® methanol-to-gasoline process. Similarly at the $CO_2$-to-methanol converter 106, typical carbon dioxide to methanol conversion methods are able to be used, such as Haldor-Topsoe.

Figure 2:
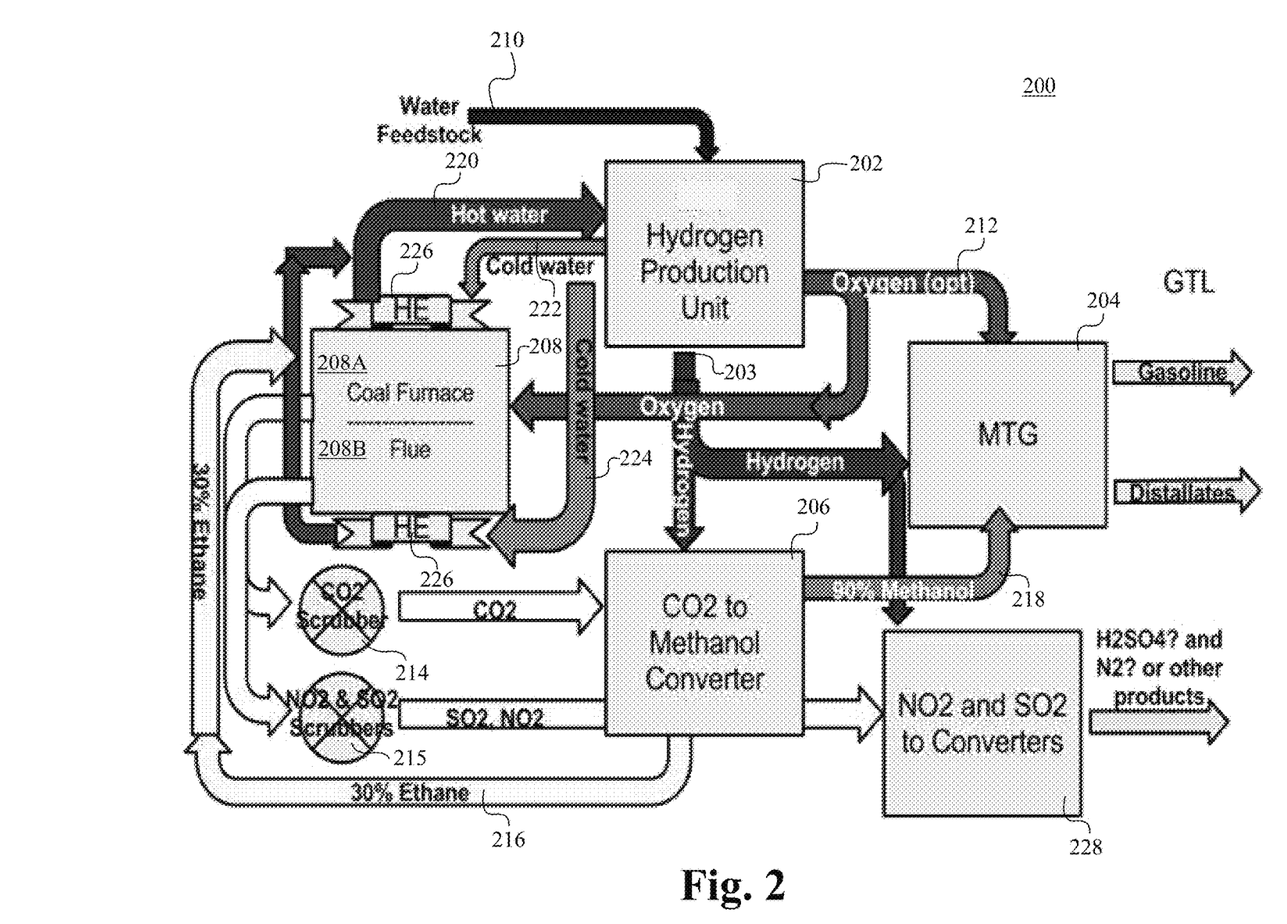
FIG. 2 illustrates a coal combustor plant for converting carbon dioxide to gasoline in accordance with some embodiments of the present invention.

FIG. 2 illustrates a coal combustor plant 200 for converting carbon dioxide to gasoline in accordance with some embodiments of the present invention. The coal combustor plant 200 comprises a hydrogen production unit 202, a methanol-to-gasoline converter (MTG converter) 204, a $CO_2$-to-methanol converter 206, and a furnace 208. The furnace 208 is able to be a coal-combustor-to-gasoline (CCTG) system, which comprises a coal furnace 208A and a flue gas chamber 208B. In some embodiments, no electricity is produced at the plant 200 but the plant 200 is able to be operated as a high efficiency GTL (gas-to-liquid) plant utilizing more than 80% of the heat generated to produce liquid fuels. The hydrogen production unit 202 receives water from the water feedstock 210 and generates hydrogen and oxygen via catalytic reactions in the hydrogen production unit 202. The reactants, reaction conditions, and the catalysts for the catalytic reactions are described below. Hydrogen 203 generated at the hydrogen generation unit 202 is supplied to the $CO_2$-to-methanol converter 206 and the MTG converter 204. Oxygen 212 that is generated at the hydrogen generation unit 202 is supplied to the furnace 208 and the MTG converter 204. The oxygen 212 that is provided to the furnace 208 facilitates the full oxygenation of COx, which is subsequently supplied to the $CO_2$-to-methanol converter 206 via a $CO_2$ scrubber 214 as a $CO_2$ source. $SO_2$ and $NO_2$ from the furnace 208 are supplied to a $NO_2$ and $SO_2$ converter 228 via a $NO_2$ and $SO_2$ scrubber 215. The $NO_2$ and $SO_2$ is able to be further converted into $H_2SO_4$ and $N_2$ at the $NO_2$ and $SO_2$ converter 228. The $CO_2$-to-methanol converter 106 generates about 10%-30% of ethane 216 that is used at the furnace 208 and about 70%-90% of methanol 218 that is supplied to the MTG 204. Hot water 220 from the furnace 208 is supplied to the hydrogen production unit 202 as a heat source. By using the waste heat from the furnace 208 as an energy source to produce hydrogen and oxygen at the hydrogen production unit 202, significant amount of energy is able to be saved. The hot water 220 that is used to heat up the hydrogen production unit 202 becomes cold water 222 and 224, which are used to cool the heat exchanger 226 at the furnace 208.

Figure 3:
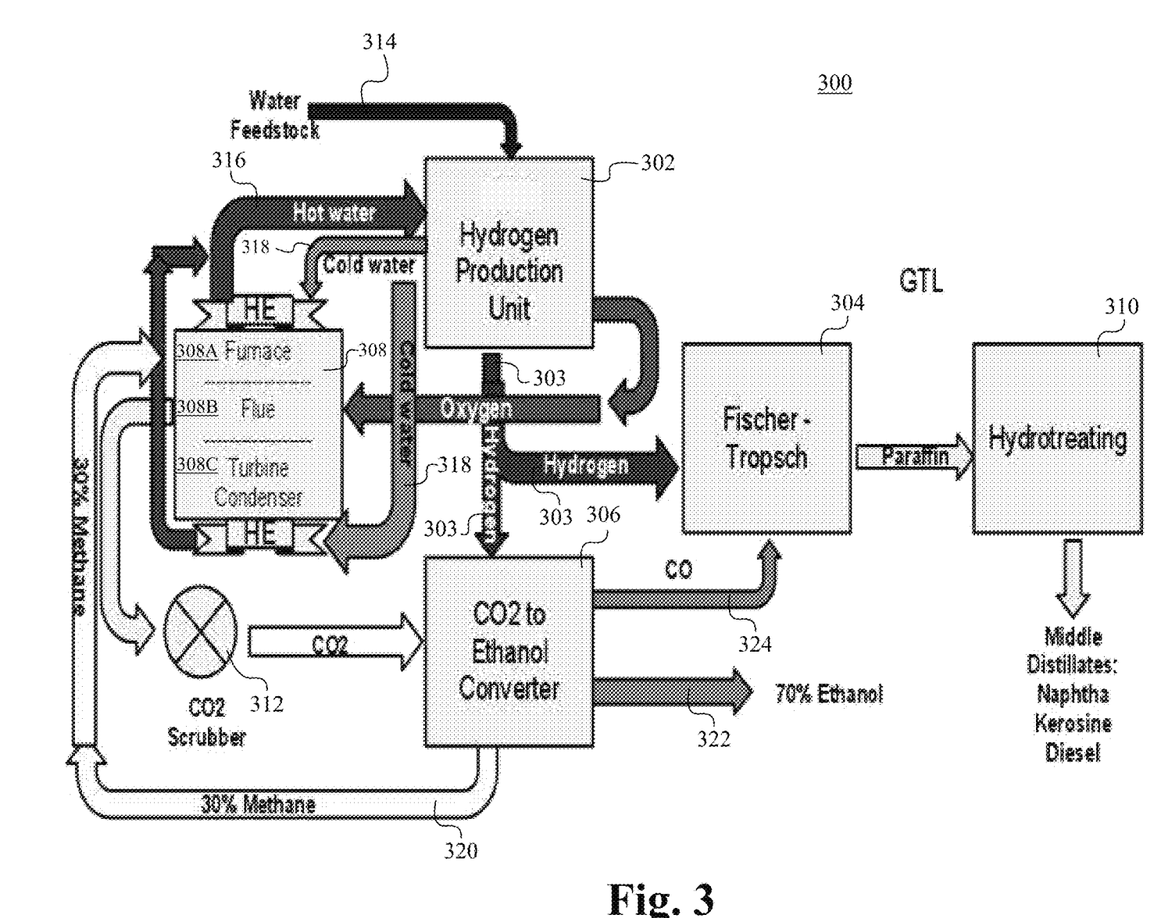
FIG. 3 illustrates a coal fired power plant for converting carbon dioxide to paraffin in accordance with some embodiments of the present invention.

FIG. 3 illustrates a coal fired power plant 300 for converting carbon dioxide to paraffin in accordance with some embodiments of the present invention. The plant 300 comprises a hydrogen production unit 302, a Fischer-Tropsch chamber 304, a $CO_2$-to-ethanol converter 306, a hydrotreating chamber 310, and a furnace 308. The furnace 308 is able to be a CFPP, which comprises a coal furnace 308A, a chamber area for flue gas 308B, and turbine and condenser 308C for generating electricity. The hydrogen production unit 302 receives water from the water feedstock 314 and generates hydrogen and oxygen via catalytic reactions in the hydrogen production unit 302. The reactants, reaction conditions, and the catalysts for the catalytic reactions are described below. Hydrogen 303 that is generated at the hydrogen generation unit 302 is supplied to the $CO_2$-to-ethanol converter 306 and the Fischer-Tropsch chamber 304. Oxygen 313 that is generated at the hydrogen generation unit 302 is supplied to the furnace 308. The oxygen 313 that is provided to the furnace 308 to facilitate the full oxygenation of COx, which is subsequently supplied to the $CO_2$-to-ethanol converter 306 via a $CO_2$ scrubber 312 as a $CO_2$ source. The $CO_2$-to-ethanol converter 306 generates about 30% of methane 320 to be used at the furnace 308. Hot water 316 from the furnace 308 is supplied to the hydrogen production unit 302 as a heat source. By using the waste heat from the furnace 308 as an energy source to produce hydrogen and oxygen at the hydrogen production unit 302, a significant amount of energy is able to be saved. The hot water 316 that is used to heat up the hydrogen production unit 302 becomes cold water 318, which is used to cool the heat exchanger 326 at the furnace 308. At the Fischer-Tropsch chamber 304, paraffin that is produced is sent to the hydro-treating chamber 310, such that the paraffin is able to be converted to naphtha, kerosene and diesel. The $CO_2$-to-ethanol converter 306 provides CO 324 to the Fischer-Tropsch chamber 304. The $CO_2$-to-ethanol converter 306 provides 70% ethanol 322.

Figure 4:
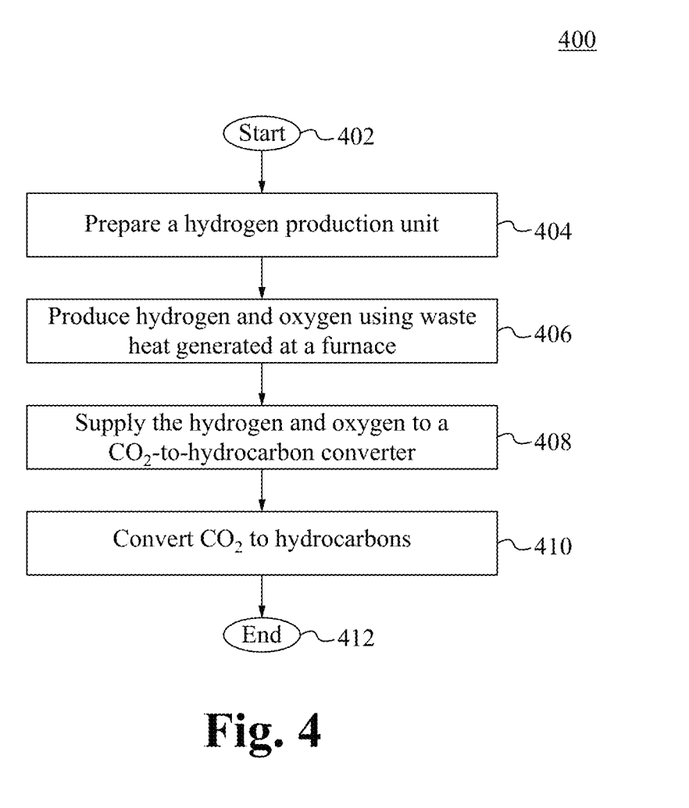
FIG. 4 is a flow chart illustrating a method of generating hydrocarbon compounds using waste heat.

FIG. 4 is a flow chart illustrating a method 400 of generating hydrocarbon compounds using waste heat. The method 400 is able to begin at Step 402. At Step 404, a hydrogen producing unit is prepared. The hydrogen producing unit contains an aluminum based catalytic system, which is described below. At Step 406, hydrogen and oxygen are produced using waste heat that is generated at a furnace. In some embodiments, the furnace comprises a Coal Fired Power Plant (CFPP), A Coal-Combustor-to-Gasoline (CCTG) Plant, or a methanol producing plant. A person of ordinary skill in the art will appreciate that any plant that generates excess heat is within the scope of the present invention, such as a nuclear power plant. At Step 408, hydrogen and oxygen produced with carbon dioxide are supplied to a hydrocarbon converter. At Step 410, carbon dioxide is converted to hydrocarbon compounds. The method stops at Step 412.

In the following, catalysts that are used in the hydrogen producing unit, such as the hydrogen production unit 102, 202, and 302 at FIGS. 1-3, are described in accordance with some embodiments of the present invention.

Example 1

The apparatus includes a main reactor, a photochemical/oxidizer reactor, and a thermal converter. The main reactor contains graphite and stainless steel parallel plates as electrodes, reactants, or catalysts. The photochemical/oxidizer reactor contains a light source, such as light, sunlight receiver, solar water heater, or other proper lights or heaters.

The conditions and procedures of performing the reactions are described in detail below. The experiment begins from catalyst preparation. In the catalyst preparation procedure, water, salts, and the starting metals including substrates of Al, Cu, and Ag are placed into a catalyst preparation vessel. Next, the starting materials are prepared by using the REDOX reaction, which is described in the following paragraph. Subsequently, the product of the catalysts preparation reaction is transferred to the main reactor. The main reactor comprises water, which is able to be prepared from tap water, distilled water, deionized water, or sea water. The salts are added to bring the salinity to 1.5% by weight using NaCl.

In the REDOX reactions, an electrical voltage is applied to the electrodes. The negative charge is connected to graphite electrodes and positive charge is connected to copper, silver, and aluminum substrates. The reactions are started by applying 1.6 volts of electricity or to the point where the Al substrate begins to liberate gas. The reactions are running for 30-40 minutes or until a clear gel suspension or heavy, white, frothy supernatant is developed. The solution is stirred occasionally until the supernatant completely dissolves into solution and forms a gelatinous suspension.

Following the catalysts preparation is the pre-generation reaction. In the pre-generation reaction, the anode in the main reactor (the stainless steel electrode) is conditioned. In some embodiments, the temperature of the reaction is set in the range from 80° F. to 130° F. The negative charge of applied electricity is connected to the stainless steel electrode and the positive charge is connected to the graphite electrode. Before applying electric voltage, the Cu, Al, and Ag metals are taken out of the solution. Next, 0.5 Volts of electricity is applied. After the current is stabilized, then voltage is added in the increments of 0.1 volts until the voltage is roughly 0.7 volts or until $H_2$ gas is produced at the stainless steel substrate. In some embodiments, it is observed that the pH value of the solution increases quickly during the pre-generation reaction.

Following the pre-generation reaction, the generation reaction is performed. In the generation reactions, the voltage is increased by 0.05 volt increments, such as 0.805V, 0.810V, and 0.815V. The voltage is continuously added to roughly 0.825 volts or until the maximum amount of the gas is generated. During this phase, hydrogen gas is produced at the stainless steel substrate. Then the voltage is reduced by 0.05 volts to find where the gas production falls off.

The hydrogen gas in the above setup is produced from the stainless steel electrode. It is observed that during the reaction, the pH value slowly increases. After the reaction, the pH of the solution decreases to about 6.5.

In some embodiments, the reaction begins with 0.22 g of Al, 0.11 g of copper and 0.17 g of silver metals, and five liters of gas is produced by using this renewable catalytic system. A person of ordinary skill in the art appreciates that an equal ratio/similar ratio scaling up to any level, such as for pilot plant or full industrial production plant, is within the scope of the present invention.

After the above reactions, the hydrogen generating substance is depleted, so the solution in the main reactor contains the depleted hydrogen generating substance and hydroxides bonded hydroxide shuttles. The solution is transferred from the main reactor to the oxidizer reactor for oxygen reaction to revive the hydroxide bonded hydroxide shuttles and hydrogen generating substance. The oxidizer reactor takes the frothy white supernatant from the main reactor and converts it to a gelatinous suspension. The gelatinous suspension contains the reactivated hydrogen generating substance, and the solution containing the gelatinous suspension is then transferred back to the main reactor. The oxidizer reactor is able to be a heat exchanger, photochemical reactor, or the thermal converter. The oxidizer reactor goes on when the pH value of the reacting solution goes up.

Example 2

The apparatus comprises a preparation reactor, a main reactor, a photochemical/oxidizer reactor, and a thermal converter. The reaction begins from preparing a solution containing Al metal 250 mg, Cu metal 250 mg, Ag metal 250 mg, a graphite electrode and 1 liter of water having 1.5% NaCl 510 by weight. A negative voltage −2.5V is applied to the graphite electrode and a first positive voltage 1.7V is applied to the Al metal for 15 minutes. Next, the first positive voltage that is applied to the Al metal is stopped, and a second positive voltage 1.4V is applied to the Cu metal for 10 minutes while the negative voltage −2.5V is concurrently applied to the graphite electrode. Next, the second positive voltage to the Cu metal is stopped, and a third positive voltage 1.0V is applied to the Ag metal for 5 minutes with the negative voltage still applied to the graphite electrode. The temperature of the solution is maintained at 88° F. In some embodiments, the procedures that are described above include the procedures of ionizing the metals into the solution. In some embodiments, the procedures are catalysts preparation.

Next, the solution is transferred into a main reaction vessel. The main reaction vessel comprises aluminium compound, copper compound, silver compound, sodium compound, and chloride compound. The term "compound" comprises all ligand states of the metal. For example, the aluminium compound include $Al^{3+}$ or $Al(OH)_x$, where the x represents the coordinated ligand numbers of the aluminium ion. In some embodiments, a voltage between 0.4V to 0.9V is applied to the cathode of the electrodes. In alternative embodiments, a voltage 0.85V is applied to the cathode of the electrodes. In other embodiments, a voltage not exceeding 0.9V is applied to the cathode of the electrodes, because it is found that hydrogen production is reduced in some experiments when a voltage exceeding 0.9V is applied. In some embodiments, the applied voltage of the anode is at 0V compared with the standard hydrogen electrode. In alternative embodiments, the anode of the electrodes is the reference electrode, which has a 0V. In some embodiments, the voltage is applied in a way that a negative charge is applied on the stainless electrode and a positive charge is applied at the graphite electrode. An electric hydrolysis reaction begins to occur when sufficient voltage is applied, and hydrogen gas is generated at the stainless electrode when the applied voltage is applied on the stainless electrode and the graphite electrode. After 30 minutes or when the amount of hydrogen gas production begins to decrease, the solution is transferred through the heater and passing through the LED lights for a photolysis reaction. Oxygen gas is collected at the outlet during the photolysis reaction. The solution is transferred back to the main reaction vessel for hydrogen production.

In some embodiments, a controlling system is connected to all components of the setup, including the catalysts preparation vessel, the main reaction vessel, the valves, the heater, the LED lights, and all electrodes. In some embodiments, the controlling system comprises computers, which are able to automate the control of each of the components of the setup. Accordingly, the controlling system is able to automate the whole electric hydrolysis process when predetermined conditions have been attended. For example, the controlling system is able to automatically initiate the reaction by applying a voltage to the preparation vessel at a trigger of a predetermined condition when hydrogen gas is needed. The controlling system is able to automatically stop the ionization process of the metals when a pre-set condition has been reached. For example, a pre-set pH value or applied voltage. Similarly, the controlling system is able to automatically transfer the solution among the various chambers or vessels by controlling the pump and the valves.

By having the controlling system, the setup is able to be controlled remotely. For example, the setup is able to be controlled by a website, through internet, telephone, or PDA. In some embodiments, the processes of the setup can be all automated at the occurring of the predetermined conditions, such as a preset timer.

Above are some embodiments of the catalytic hydrogen/oxygen producing systems of the present invention. U.S. patent application Ser. No. 12/706,639, filed Feb. 16, 2010, and entitled "Method and Apparatus for Efficient On-demand Production of $H_2$ And $O_2$ From Water Using Waste Heat and Environmentally Safe Metals", which claims priority from U.S. Provisional Patent Application Ser. No. 61/154,282, filed Feb. 20, 2009 and entitled "Method and Apparatus for Efficient On-demand Production of $H_2$ And $O_2$ From Water Using Environmentally Safe Metals", which are all hereby incorporated herein by reference in their entirety for all purposes. Further, U.S. patent application Ser. No. 13/366,216, filed Feb. 3, 2012 and entitled "Stability Control of a Hydrogen Generating System and Method," which is hereby incorporated herein by reference in its entirety for all purposes.

To utilize the on-site excess heat at a power plant, the excess heat heats up water to be transported to the hydrogen producing unit as an energy source to increase a hydrogen and oxygen producing rate.

In operation, the hydrogen production unit produces hydrogen and oxygen, which are supplied to $CO_2$-to-methanol converter, the methanol-to-gasoline converter, and/or the hydrocarbon compound converter, such that carbon dioxide are able to be converted to hydrocarbons.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A system for producing hydrocarbon compounds comprising:
    a. a hydrogen producing unit containing a hydrogen producing catalyst having aluminum, copper, and silver;
    b. a coal furnace producing heat and carbon dioxide, wherein the coal furnace receives oxygen from the hydrogen producing unit, wherein the coal furnace supplies hot water to heat up the hydrogen producing unit and the hot water becomes cold water to circulate back from the hydrogen producing unit to cool a heat exchanger at the coal furnace;
    c. a hydrocarbon converter, wherein the hydrocarbon converter receives hydrogen from the hydrogen producing unit; and
    d. a methanol converter coupled with the hydrogen producing unit, wherein the methanol converter receives hydrogen from the hydrogen producing unit, separately receives the carbon dioxide from the coal furnace, and outputs an amount of 10%-30% of ethane to the coal furnace and 70%-90% of methanol to the hydrocarbon converter, wherein the ethane generates heat at the coal furnace as a source of heat for the hydrogen producing unit, wherein the hydrogen from the hydrogen producing unit is split into a first portion for supplying to the methanol converter and a second portion for supplying to the hydrocarbon converter.

2. The system of claim 1, wherein the furnace comprises a coal fired power plant.

3. The system of claim 1, wherein the furnace comprises a coal-combustor.

4. The system of claim 1, wherein the methanol converter comprises a $CO_2$-to-methanol converter.

5. The system of claim 1, wherein the hydrocarbon converter comprises a methanol-to-gasoline converter.

6. The system of claim 1, wherein the heat generates the hot water to be supplied to the hydrogen producing unit.

7. A system for producing hydrocarbon compounds comprising:
   a. a hydrogen producing unit containing a hydrogen producing catalyst having aluminum, copper, and silver;
   b. a coal furnace producing heat and carbon dioxide, wherein the coal furnace receives oxygen from the hydrogen producing unit, wherein the coal furnace supplies hot water to heat up the hydrogen producing unit and the hot water becomes cold water to circulate back from the hydrogen producing unit to cool a heat exchanger at the coal furnace;
   c. a hydrocarbon converter, wherein the hydrocarbon converter receives hydrogen from the hydrogen producing unit; and
   d. an ethanol converter coupled with the hydrogen producing unit, wherein the ethanol converter receives hydrogen from the hydrogen producing unit, separately receives the carbon dioxide from the coal furnace, and outputs an amount of 30% methane to the coal furnace and carbon monoxide to the hydrocarbon converter, wherein the methane generates heat at the coal furnace as a source of heat for the hydrogen producing unit, wherein the hydrogen from the hydrogen producing unit is split into a first portion for supplying to the ethanol converter and a second portion for supplying to the hydrocarbon converter.

8. The system of claim 7, wherein the furnace comprises a coal fired power plant.

9. The system of claim 7, wherein the furnace comprises a coal-combustor.

10. The system of claim 7, wherein the ethanol converter comprises a $CO_2$-to-ethanol converter.

11. The system of claim 7, wherein the heat generates the hot water to be supplied to the hydrogen producing unit.

12. The system of claim 7, wherein the hydrocarbon converter comprises a Fischer-Tropsch processing unit.

13. The system of claim 7, wherein the hydrocarbon converter comprises a paraffin producing unit.

14. The system of claim 7, wherein the hydrocarbon converter comprises a naphtha, kerosene, or diesel producing unit.

* * * * *